United States Patent [19]

Gramlich et al.

[11] Patent Number: 4,918,205
[45] Date of Patent: Apr. 17, 1990

[54] PREPARATION OF ALKYLATED DODECHYDRONAPHTO[2,1-B]FURANS

[75] Inventors: Walter Gramlich, Edingen-Neckarhausen; Eckhard Hickmann, Dannstadt-Schauernheim; Rainer Becker, Bad Durkheim; Gerald Lauterbach, Ludwigshafen, all of Fed. Rep. of Germany

[73] Assignee: BASF Aktiengesellschaft, Ludwigshafen, Fed. Rep. of Germany

[21] Appl. No.: 250,077

[22] Filed: Sep. 28, 1988

[30] Foreign Application Priority Data

Sep. 30, 1987 [DE] Fed. Rep. of Germany ....... 3732954

[51] Int. Cl.$^4$ ........................................... C07D 307/92
[52] U.S. Cl. ..................................................... 549/458
[58] Field of Search ........................................ 549/458

[56] References Cited

FOREIGN PATENT DOCUMENTS

| | | | |
|---|---|---|---|
| 0165458 | 12/1985 | European Pat. Off. ............ | 549/458 |
| 204009 | 12/1986 | European Pat. Off. ............ | 549/458 |
| 860214 | 7/1949 | Fed. Rep. of Germany ...... | 549/458 |
| 3240054 | 5/1984 | Fed. Rep. of Germany ...... | 549/458 |
| 432815 | 1/1976 | Spain ................................. | 549/458 |
| 345153 | 8/1972 | U.S.S.R. ............................ | 549/458 |
| 529166 | 4/1977 | U.S.S.R. ............................ | 549/458 |
| 910561 | 3/1982 | U.S.S.R. ............................ | 549/458 |
| 988817 | 1/1983 | U.S.S.R. ............................ | 549/458 |

OTHER PUBLICATIONS

Dehmlow, et al., Phase Transfer Catalysis, Verlag Chemie, Deerfield Beach, FL, 1980, p. 88.
Fragrance Chemistry, Academic Press, (1982), p. 542, G. Ohloff.
Helvetica Chimica Acta, vol. 68, (1985), pp. 2022–2028, G. Ohloff.
Fortschritte Chem. Forsch. 12/2, (1969), pp. 185–251, G. Ohloff.
Maslo-Zhir, Promst. 1979, (12), pp. 25–26, V. E. Sibiertseva.
Dragoco-Report, 11/12, (1979), pp. 276–283, E. J. Brunke.
Austr. Journal of Chemistry, vol. 24, (1971), pp. 583–91, and 2365–77, R. C. Cambie.
Syntheses, (1983), pp. 816–818, G. Aumaitre, et al.
Angew. Chemie, vol. 89, (1977), pp. 521–533, Dehmlow.
Angew. Chemie, vol. 86, (1974), pp. 187–196.

*Primary Examiner*—Mary C. Lee
*Assistant Examiner*—Robert C. Whittenbough
*Attorney, Agent, or Firm*—Oblon, Spivak, McClelland, Maier & Neustadt

[57] ABSTRACT

Alkylated dodecahydronaphtho[2,1-b]furans of the general formula I

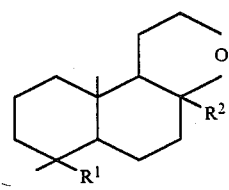

(I)

where $R^1$ and $R^2$ are identical and each is hydrogen or methyl are prepared by reacting alkylated 2-hydroxydecahydronaphthalene-1-ethanol of the formula II

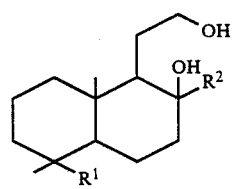

(II)

where $R^1$ and $R^2$ are as defined above, with a sulfonyl chloride in the presence of basic catalysts by performing the cyclization in the presence of concentrated aqueous alkali metal hydroxides and a phase transfer catalyst, preferably a tetra-substituted ammonium or phosphonium salt, the sulfonyl chloride used preferably comprising a sulfonyl chloride of the general formula III $R_3\text{-}SO_2Cl$ where $R^3$ is $C_1$-$C_3$-alkyl or phenyl which may be substituted in the para position by methyl, chlorine, bromine or nitro.

9 Claims, No Drawings

PREPARATION OF ALKYLATED DODECHYDRONAPHTO[2,1-B]FURANS

A compound having the basic structure of dodecahydronaphtho[2,1-b]furan of the formula I

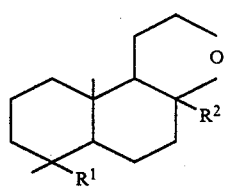

where $R^1$ and $R^2$ are identical, each being methyl, is in the form of an enantiomer ([3aR-(3aα,5aβ,9aα,9bβ)]) an ambergris scent used for decades in perfumery (Ambrox® from Firmenich; Ambroxan® from Henkel).

This ambergris scent, besides occurring in the ambergris tincture of the sperm whale, has in the meantime also been found in clary sage oil (Salvia sclarea L.), in labdanum oil (Cistus labdaniferus L.) and also in cypress oil (Cupressus semperoirens L.) (cf. G. Ohloff in Fragrance Chemistry, Academic Pre$s, 1982, p. 543). It is responsible for the ambergris effect, which is desirable in perfume compositions, acting even in high dilution, and also for excellent fixation even of delicate, floral fragrances. It is used mainly in expensive perfume oils.

The four diastereoisomers of this ambergris scent (formula I, $R^1$, $R^2$=CH₃)

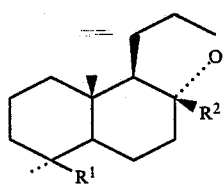
(Ia)

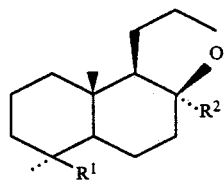
(Ib)

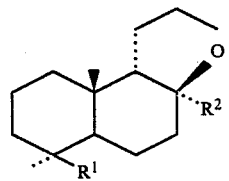
(Ic)

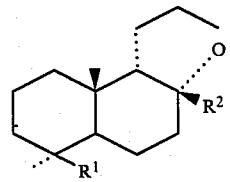
(Id)

Ia-Id differ clearly from one another. For instance, the scent of Isoambrox (Ib) is over one hundred times weaker than that of the compound of the formula Ia (cf. G. Ohloff et al., Helv. Chim. Acta, 68 (1985), 2022–29), and the scent of Norisoambrox (formula Ib where $R^1$=H and $R^2$=CH₃) is more than 500 times weaker than that of the compound of the formula Ia.

The ambergris scent of the formula Ia ($R^1$, $R^2$=CH₃) and the diastereoisomer mixtures of the formulae Ia to Id can be prepared not only partially synthetically from ambrein or diterpenes of the labdanum type (for example sclareol, manool) but also by total synthesis (cf. review by E.-J. Brunke, Dragoco Report, 11/12-1979, 276 ff).

On an industrial scale, the ambergris scent is chiefly produced by oxidative degradation (chromic acid, permanganate, ozone) of sclareol, an ingredient of clary sage concretes. The sclareolide obtained as degradation product is converted, by lithium alanate or sodium boronate reduction, into a 1,4-diol (ambroxdiol) which is subsequently cyclized (cf. G. Ohloff, Fortschr. Chem. Forsch. 12/2 (1969), 185 ff):

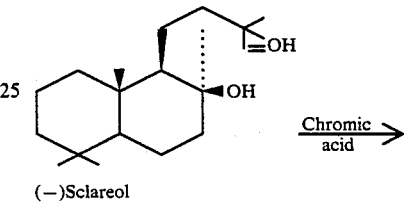
(−)Sclareol

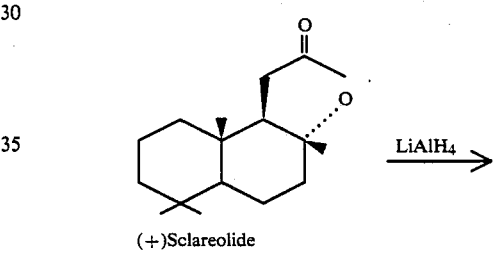
(+)Sclareolide

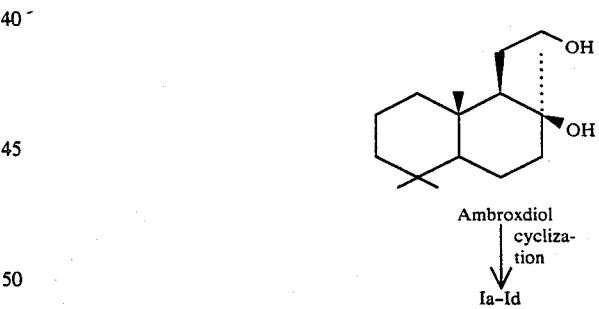
Ambroxdiol cyclization
Ia-Id

Because, of the four diastereoisomers, the compound of the formula Ia has the greatest olfactory importance, there is much prior art concerned with performing the last step, the cyclization, with high selectivity.

For instance, V. E. Sibiertseva et al. describe in Maslo-Zhir, Prom.-st. 1979 (12), 25–26, the cyclization of ambroxiol in the presence of p-toluenesulfonic acid. The disadvantage with this process is the unavoidable, in an acid medium, dehydration of the tertiary hydroxyl group, leading to selectivity losses. Also the reported yields of from 55 to 60% are unsatisfactory for an industrial process, in particular with regard to the costly educt.

The use of p-toluenesulfonic acid is also claimed in the processes of Soviet Patents 345-153 (dated 1968), 910-561 (dated 1980) and 529-166 (dated 1975).

In the process of an earlier patent to Firmenich (German Patent No. 860,214 dated 1949), the catalysts described are naphthalenesulfonic acid (78% yield) and aluminum oxide (50% yield). Here too the abovementioned disadvantages, such as poor selectivity and also unsatisfactory yields were observed.

In the process of Spanish Patent No. 432,815 (dated 1976), the cyclization of ambroxdiol is carried out with sulfuric acid; the yields obtained were only of the order of 29%.

R. C. Cambie et al. describe in Aust. J. Chem. 24 (1971), 583–591, 2365–2377, the cyclization of ambroxdiol by means of p-toluenesulfonyl chloride and pyridine with an 80% yield. The main disadvantages in this case are the nauseous odor of pyridine, bearing in mind the need to refine the quality of the scent obtained, and the relatively long reaction times. In addition, in the aqueous workup it is necessary to recycle the pyridine on account of its solubility in water, which increases costs.

In a second method of cyclization Cambie used sulfuric acid as the catalyst. In this case the disadvantages were the long reaction time (3 days) and the poor yields (43% of theory).

Anhydrous pyridine is again the medium in the POCl$_3$-based cyclization method described by Consertium Elektrochemie in German Laid-Open application DOS No. 3,240,054 (dated 1982), and the disadvantges here are therefore the same as described above. The yields were only 65% of theory.

P. F. Vead and N. D. Unger described in Synthesis, 1983, 816–18, a method of cyclization where the reagent used was trimethylchlorosilane in dimethyl sulfoxide (DMSO); the yields reported here were 85%. As is evident from the experimental example given therein, this method is only a laboratory method (mg batches). Industrially, the use of DMSO is a disadvantage, since, following the aqueous workup, its watersolubility (and potential effluent problems) necessitate expensive recycling. A decisive disadvantage in addition is the need to purify the crude ambergris scent obtained in the reaction to a both chemically and olfactorily acceptable quality. The chemical purification was done by costly column chromatography, complete removal of DMSO being difficult in most cases. A further problem is the industrially frequently difficult handling of trimethylchlorosilane, which is highly corrosive and also toxicologically unsafe.

The same method of cyclization is also described in Soviet Patent No. 988,817 (dated 1980).

Furthermore, EP-A-204,009 discloses a process for preparing Ambro® where sclareol is converted biotechnically into ambroxdiol which is cyclized to the dodecahydro-3a,6,6,9a-tetramethylnaphtho[2,1-b]furan of the formula I. The cyclization is effected with an arylsulfonyl chloride in the presence of acidic compounds, such as HCl and acid ion exchangers, or in the presence of bases, such as pyridine and NaOH. This cyclization in an acid medium gives poor yields. The disadvantages of a cyclization in the presence of organic bases, such as pyridine on an industrial scale, were described in detail above.

The cyclization using sulfonyl chlorides in the presence of alkali metal hydroxides is relatively successful. The disadvantages here, however, are the relatively long reaction times, the still inadequate purities of the compounds of the formula I obtained, and the partly high reaction temperature which can lead to selectivity losses (cf. Example 9).

It is an object of the present invention to provide a highly selective method of cyclization which is easy to put into effect in industry and which leads to an olfactorily suitable product without the disadvantages described.

We have found, surprisingly, that this object is achieved, and that the cyclization of ambroxdiol is possible without the abovementioned disadvantages of existing processes, when the diol is cyclized in an organic solvent using a sulfonyl chloride and an aqueous alkali metal hydroxide in the presence of a phase transfer catalyst.

To our knowledge the cyclization of a 1,4-diol with a sulfonyl chloride is the first example of a tetrahydrofuran synthesis in the presence of a phase transfer catalyst. Reviews concerning the reactions in the presence of phase transfer catalysts: E. V. Dehmlow and S. S. Dehmlow: Phase Transfer Catalysis, Verlag Chemie, 1980; in particular E. V. Dehmlow in Angew. Chemie 89 (1977), 521f, and Angew. Chemie 86 (1974), 187 f.

The present invention accordingly provides a process for preparing an alkylated dodecahydronaphtho[2,1-b]furan of the general formula I

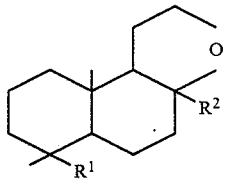

I where R$^1$ and R$^2$ are identical and each is hydrogen or methyl, by reacting an alkylated 2-hydroxydecahydronaphthalene-1-ethanol of the formula II

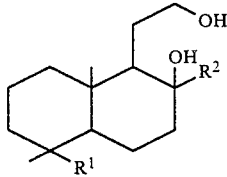

II where R$^1$ and R$^2$ are each as defined above, with a sulfonylchloride in the presence of a basic catalyst by performing the cyclization in the presence of a concentrated aqueous alkali metal hydroxide and of a phase transfer catalyst.

The selectivity surprisingly obtained with the process according to the invention is above 95%, complete conversion being obtained at the same time; this 10% yield increase over the best prior art constitutes a significant reduction in costs, given the high cost of the starting compound.

Moreover, sclareol which is most commonly used in industry as the starting compound is only available to a limited extent and as a natural product is subject to frequently large fluctuations in harvest volume due to the weather. The more than 10% increase in yield therefore reduces the amount of the costly starting sclareol required.

A further, highly significant advance over existing ring closure reactions carried out in the presence of pyridine is the significantly simpler workup and purification of the product to give an olfactorily acceptable ambergris scent. This is because, as the ambergris note is marked by a warm, delicate, erotic balsam fragrance, even small impurities in the scent are highly noticeable.

The selectivities obtained in the process according to the invention are very good.

For this reason the purification of the product produced by the novel process according to the invention does not present any problems either.

The process according to the invention can be carried out with any one of a large number of phase transfer catalysts (general survey cf. V. Dehmlow, Angew. Chemie. 89 (1977), 521–33). Particularly preferred as phase transfer catalysts are: 1. tetraalkylammonium salts of the general formula IV

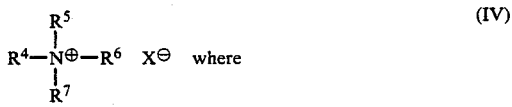

(IV)

$R^4$, $R^5$, $R^6$ and $R^7$ may be identical to or different from one another and each may be alkyl of from 1 to 22 carbon atoms or alkyl of up to 25 carbon atoms containing functional groups such as hydroxyl, carboxamide or ether groups, such as methyl, ethyl, (iso)propyl, butyl, octyl, dodecyl, $C_{16}H_{33}$-, hydroxy(iso)propyl or

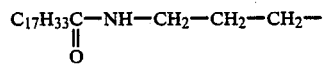

or may be phenyl or phenyl substituted alkyl (e.g. benzyl) of up to 20 carbon atoms, and $X^{\ominus}$ is an anion of an acid such as $I^-$, $Cl^-$, $Br^-$, $(HSO_4)^-$, $(CN)^-$ or $(BF_4)^-$, in particular the very inexpensive trimethylbenzylammonium chloride, which can be used in the form of its 50% strength aqueous solution, and also tricaprylomethylammonium chloride; and 2. tetraalkylphosphonium salts of the general formula V

(V)

where $R^4$, $R^5$, $R^6$, $R^7$ and $X^{\ominus}$ are as defined for the formula (IV), in particular tri-n-octylmethylphosphonium iodide.

Also suitable are mixtures of the abovementioned phase transfer catalyst and support-fixed phase transfer catalysts.

The phase transfer catalysts are used for the process according to the invention in amounts of from 0.1 to 1, preferably from 0.3 to 0.5, mole per mole of diol.

The solvents suitable for the phase transfer catalyst reaction depend on the solubility of the diol to be used; suitable are inter alia dichloromethane, tetrahydrofuran, dioxane, benzene, toluene and xylene.

Suitable basic catalysts are concentrated aqueous alkali metal hydroxides, in particular aqueous sodium hydroxide and potassium hydroxide solutions. The amount of solution used is less critical. It can vary from 2 to 8 moles per mole of diol used. A particularly rapid cyclization is obtained with an approximate molar excess of the alkali metal hydroxide solution, based on the diol (total reaction time ~1 h). If the amount of alkali metal hydroxide solution used is reduced, the rate of reaction decreases. An increase in the amount of alkali metal hydroxide solution is uneconomical, since the already short reaction time cannot be cut any further.

Suitable sulfonyl chlorides are the known reagents for substitution reactions such as methanesulfonyl chloride, ethanesulfonyl chloride, benzenesulfonyl chloride, p-toluenesulfonyl chloride, p-chloro- or p-bromo-benzenesulfonyl chloride and p-nitrobenzenesulfonyl chloride, i.e. sulfonyl chlorides of the general formula III

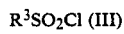 (III)

where $R^3$ is $C_1$-$C_3$-alkyl or phenyl which may be substituted in the para position by methyl, chlorine, bromine or nitro.

The diols of the general formula II used as starting materials are obtainable by known literature methods (cf. G. Ohloff et al., Helv. Chim. Acta 68 (1985), 2022–29).

By means of the process according to the invention, the dodecahydronaphtho[2,1-b]furans of the general formula I desirable for use as ambergris scents are preparable in a simple manner in relatively short reaction times in selectivities of up to 95% with complete conversion.

The following Examples will describe the process according to the invention in more detail:

EXAMPLE 1

Preparation of [3aR-(3aα,5aβ,9aα,9bβ)]dodecahydro-3a,6,6,9a-tetramethylnaphtho[2,1-b]furan (Formula Ia ($R^1$, $R^2$=methyl)

142 g (0.56 mol) of decahydro-2-hydroxyl-2,5,5,8a-tetramethyl-1-naphthaleneethanol, prepared from sclareolide (dodecahydro-3a,6,6,9a-tetramethylnaphtho-[2,1-b]-furan-2-one, mp. 124° C., $[a]^{20}_D = +48°$ C., from Reynolds/USA) by the method of M. Hinder and M. Stoll, Helv. Chim. Acta 36 (1953), p. 1995–2008 (mp. 132° C.), were dissolved in 2,110 g (2,434 ml) of toluene. 200 ml (304 g) of 50% strength sodium hydroxide solution (3.8 mol) were then added dropwise at 25° C., followed by 86 ml of a 50% strength aqueous solution of benzyltrimethylammonium chloride (0.2 mol). 105 g (0.6 mol) of benzenesulfonyl chloride were added dropwise in the course of one hour (1 h) with slight cooling, and the reaction mixture was subsequently stirred for 2 hours (analysis by thin layer chromatography showed complete conversion).

To work up the mixture, 500 ml of water were added dropwise, the mixture was subsequently stirred for 15 minutes and then left to stand for 1 hour, and the phases were then separated.

The bottom phase was separated off, the top, toluene-containing phase was flushed once more with 250 ml of water, and then the toluene was distilled off at 400 mbar. The remaining residue was distilled under substantially reduced pressure (bp. 100° C./0.006 mbar).

126.2 g were obtained of [3aR-(3a,5a,9a,9b]-dodecahydro-3a,6,6,9a-tetramethylnaphtho[2,1-b]furan, which corresponds to a yield of 95.5% (GC purity: 99.9%; mp. 76–77° C., $[a]^{25}_D = 26.3°$ ).

EXAMPLE 2

Preparation of isoambrox (formula Ib where $R^1$, $R^2 = CH_3$)

Isomerization and subsequent lithium alanate reduction of sclareolide by the method of G. Ohloff, Helv. Chim Acta, 68 (1985), 2022-29, was used to obtain a diastereoisomeric decahydro-2-hydroxy-2,5,5,8a-tetramethyl1-naphthaleneethanol (mp. 191° C.). 142 g of this diol were dissolved in 2,110 g of toluene, and the solution was admixed with 120 g (3 mol) of sodium hydroxide in 120 ml of water and then with 48 g (0.15 mol) of tetrabutylammonium bromide. 101 g (0.5 mol) of p-toluenesulfonyl chloride were then added twice in the course of 1 hour, and the reaction mixture was subsequently stirred for 2 hours, and admixed with 500 ml of water and thereafter thoroughly stirred for a further 10-20 minutes. The bottom, aqueous phase was separated off and washed once with 200 ml of water, and thereafter the solvent was distilled off at 300 mbar. Recrystallization of the residue left 121.6 g of isomeric dodecahydro-3a,6,6,9a-tetramethylnaphtho[2,1-b]furan (formula Ib; $R^1$, $R^2=CH_3$), of mp. 60° C. and $[\alpha]^{20}_D = +7.5°$, which corresponds to a yield of 92%.

We claim:

1. A process for preparing an alkylated dodecahydronaphtho (2,1-b) furan of the formula (I):

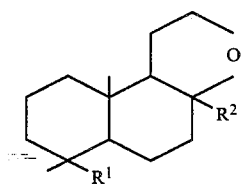

wherein $R^1$ and $R^2$ are identical and each is hydrogen or methyl, which comprises reacting an alkylated 2-hydroxydecahydronaphthalene-1-ethanol of the formula (II):

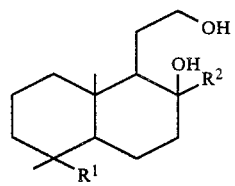

wherein $R^1$ and $R^2$ are each as defined above, with a sulfonyl chloride in the presence of a basic catalyst by performing the cyclization in the presence of a concentrated aqueous alkali metal hydroxide and a phase transfer catalyst, wherein said phase transfer catalyst is a tetraalkylammonium salt of the formula (IV):

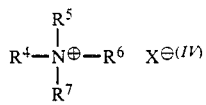

wherein $R^4$, $R^5$, $R^6$ and $R^7$ are identical to or different from each other and are independently alkyl of from 1 to 22 carbon atoms or alkyl of up to 25 carbon atoms, which carbon atoms are unsubstituted or substituted by hydroxyl, carboxamide or ether groups, or each of $R^4$, $R^5$, $R^6$ and $R^7$ are phenyl or phenyl substituted with alkyl groups of up to 20 carbon atoms, and wherein $X^-$ is an anion of an acid; or said phase transfer catalyst is a tetraalkylphosphonium salt of the formula (V):

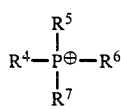

wherein $R^4$, $R^5$, $R^6$, $R^7$ and $X^{31}$ are as defined above for the formula (IV).

2. The process as claimed in claim 1, wherein $X^{31}$ is an anion of an acid selected from the group consisting of $I^-$, $Cl^-$, $Br^-$, $(HSO_4)^-$, $(CN)^-$ or $(BF_4)^-$.

3. The process as claimed in claim 1, wherein the phase transfer catalyst is tri-n-octylmethylphosphonium iodide.

4. The process as claimed in claim 1, wherein the phase transfer catalyst is trimethylbenzylammonium chloride or tricaprylmethylammonium chloride.

5. The process as claimed in claim 1, wherein said sulfonyl chloride has the formula (III):

$$R^3-SO_2Cl \qquad (III)$$

wherein $R^3$ is $C_1$-$C_3$-alkyl, phenyl or phenyl which is substituted in the para position by methyl, chlorine, bromine or nitro.

6. The process as claimed in claim 1, wherein said phase transfer catalyst is used in an amount of about 0.1 to 1 mole per mole of diol.

7. The process as claimed in claim 5, wherein said phase transfer catalyst is used in an amount of about 0.3 to 0.5 mole per mole of diol.

8. The process as claimed in claim 1, wherein said alkali metal hydroxide is sodium hydroxide or potassium hydroxide and is used in an amount of about 2 to 8 moles per mole of diol.

9. The process as claimed in claim 1, wherein said sulfonyl chloride of the formula (III) is selected from the group consisting of methanesulfonyl chloride, ethanesulfonyl chloride, benzenesulfonyl chloride, p-toluenesulfonyl chloride, p-chloro- or p-bromobenzenesulfonyl chloride and p-nitrobenzenesulfonyl chloride.

* * * * *